(12) United States Patent
Voix et al.

(10) Patent No.: US 9,216,114 B2
(45) Date of Patent: Dec. 22, 2015

(54) HEAD-MOUNTED DEVICE FOR SETTABLE COMPOUND DELIVERY SYSTEM FOR INFLATABLE IN-EAR DEVICE

(75) Inventors: Jérémie Voix, Montreal (CA); Michael C. Turcot, Montreal (CA); Katrin Braun, Montreal (CA); Steve Boa, Montreal (CA); Lawrence Yane, Montreal (CA)

(73) Assignee: SONOMAX TECHNOLOGIES INC., Montréal, Québec (CA)

( * ) Notice: Subject to any disclaimer, the term of this patent is extended or adjusted under 35 U.S.C. 154(b) by 568 days.

(21) Appl. No.: 12/929,094

(22) Filed: Dec. 30, 2010

(65) Prior Publication Data

US 2011/0158456 A1    Jun. 30, 2011

Related U.S. Application Data

(60) Provisional application No. 61/282,213, filed on Dec. 31, 2009.

(51) Int. Cl.
| | |
|---|---|
| *A61F 11/06* | (2006.01) |
| *A61F 11/08* | (2006.01) |
| *A61F 11/10* | (2006.01) |
| *A61F 11/12* | (2006.01) |
| *A61F 11/00* | (2006.01) |

(52) U.S. Cl.
CPC .................. *A61F 11/12* (2013.01); *A61F 11/00* (2013.01); *A61F 11/06* (2013.01); *A61F 11/08* (2013.01); *A61F 11/10* (2013.01)

(58) Field of Classification Search
CPC ......... A61F 11/00; A61F 11/06; A61F 11/08; A61F 11/10; A61F 11/12; A61F 11/14; A61C 5/06; A61C 5/062; A61C 5/064; A61C 5/068; A61C 9/0026
USPC .......... 128/857, 864–866; 181/129–130, 135; 381/328, 380; 433/80–90
See application file for complete search history.

(56) References Cited

U.S. PATENT DOCUMENTS

| | | | | |
|---|---|---|---|---|
| 3,110,356 | A * | 11/1963 | Mendelson | 181/130 |
| 3,301,253 | A * | 1/1967 | Glorig | 128/866 |
| 3,505,999 | A * | 4/1970 | Harvey et al. | 128/865 |
| 3,841,326 | A * | 10/1974 | Leight | 128/866 |
| 4,682,363 | A * | 7/1987 | Goldfarb et al. | 381/74 |
| 4,896,380 | A * | 1/1990 | Kamitani | 2/428 |
| 4,896,679 | A * | 1/1990 | St. Pierre | 128/865 |
| 4,913,165 | A * | 4/1990 | Fishgoyt | 128/865 |
| 6,339,648 | B1 | 1/2002 | McIntosh et al. | |

(Continued)

FOREIGN PATENT DOCUMENTS

| | | |
|---|---|---|
| EP | 1 971 179 A1 | 9/2008 |
| WO | WO 02/07477 A2 | 1/2002 |

*Primary Examiner* — Alireza Nia
*Assistant Examiner* — Camtu Nguyen
(74) *Attorney, Agent, or Firm* — Equinox IP; Franz Bonsang

(57) ABSTRACT

A head-mounted support device for carrying at least one un-inflated inflatable or expandable inner portion of an in-ear device thereon includes a main body adjustably mountable on a user's head, with at least one settable compound delivery device mounted thereon, and a at least one receptacle to receive an inflatable in-ear device inner portion. The invention also refers to a head-mounted settable compound delivery system kit, along with the earphone wire assembly that receives the customized in-ear device inner portions thereon.

8 Claims, 3 Drawing Sheets

(56) References Cited

U.S. PATENT DOCUMENTS

| | | | |
|---|---|---|---|
| 6,500,001 B2 * | 12/2002 | Horth et al. ............ 433/89 |
| 6,513,621 B1 * | 2/2003 | Deslauriers et al. ........ 181/130 |
| 6,754,357 B2 | 6/2004 | McIntosh et al. |

* cited by examiner

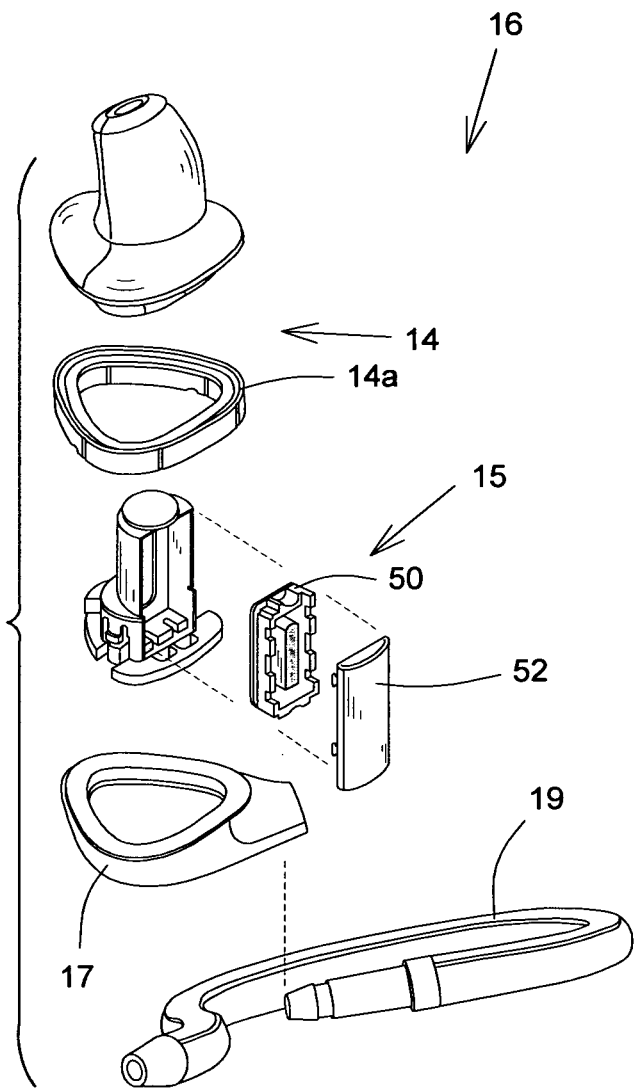

HEAD-MOUNTED DEVICE FOR SETTABLE COMPOUND DELIVERY SYSTEM FOR INFLATABLE IN-EAR DEVICE

CROSS REFERENCE TO RELATED APPLICATIONS

Benefit of U.S. Provisional Application for Patent Ser. No. 61/282,213 filed on Dec. 31, 2009, which is incorporated herein by reference, is hereby claimed.

FIELD OF THE INVENTION

This invention relates to in-ear devices, such as intra-aural hearing protectors (earplugs), earphones, or hearing-aide devices, which are inflatable to provide proper fit within the ear canal and particularly to head-mounted support devices for injection of a settable compound into the in-ear devices while holding the in-ear devices in proper positions into the corresponding user's outer ear canal.

BACKGROUND OF THE INVENTION

The term in-ear device includes active as well as passive devices in which all or at least a portion of the device is inserted into the ear canal of the user. The devices may include means for generation, amplification or suppression of sound. Such devices are described in U.S. Pat. Nos. 6,754,357 and 6,339,648 (both of which are herein incorporated in their entirety) in which a rigid or semi-rigid central core component is provided with an expandable sheath over the innermost portion of the device.

In order to ensure a proper inflation of the expandable sheath, a settable compound delivery system or apparatus, as described in co-pending U.S. patent application Ser. No. 12/923,696 and Ser. No. 12/923,698 filed on Oct. 5, 2010 (both of which are herein incorporated in their entirety), along with an inner portion of an in-ear device as described in co-pending U.S. patent application Ser. No. 12/923,697 filed on Oct. 5, 2010 (which is also herein incorporated in its entirety), is best suited for use by the user himself/herself. Nonetheless, to this end, a support device is required for the user's self-customization of the in-ear devices.

In areas of application in the industry, it is important to obtain proper fitment for achieving consistent results in both hearing aid, hearing protection applications, and dedicated sound transmission devices, without the involvement of a trained technician.

Accordingly, there is a need for an improved head-mounted support device for carrying a settable compound delivery system for an inflatable in-ear device.

BRIEF SUMMARY OF THE INVENTION

Accordingly, as a general object the invention concerns an improved head-mounted support device for carrying a settable compound delivery system for injecting the compound into an inflatable in-ear device.

An advantage of this invention is that it provides a head-mounted support device which is easily adjustable by the user on his/her head for proper positioning of the un-inflated inflatable in-ear devices prior to customizing the same, without requiring the involvement of a trained technician.

Another advantage of this invention is that it provides a head-mounted support device compact unitary system for providing customized installation of an in-ear device.

A further advantage of this invention is that it provides a head-mounted support device that allows for a proper orientation of the inflatable in-ear device(s), or inner portion(s) thereof, typically at a preferred frontward and upward angular orientation, optionally using a restricted biased gimbal connection, while maintaining the required target pressure on the in-ear device(s), or inner portion(s) thereof, during inflation thereof.

Still another advantage of this invention is that it provides a head-mounted support device that removably carries settable compound delivery systems and preferably inner portions of inflatable in-ear devices, for repeated use of the same for different sets of in-ear devices, whenever required.

A further advantage of this invention is that the head-mounted support device can be used and activated by the user himself following a step-by-step sequence of instructions, which could include a sound hearing adjustment, or sound delivery system, in situ to help proper positioning of in-ear devices just prior to the settable compound injection therein.

Yet another advantage of this invention is that the head-mounted support device includes a main support structure positionable, and preferably adjustable, onto the head of the user in order to be integral therewith, such as a headband or the like.

Yet another advantage of this invention is that the head-mounted support device is part of a kit that also includes an earphone wire assembly for mounting the inflated and customized inner portion of the in-ear device onto an outer portion of an in-ear device, preferably including a removable/interchangeable active component therein (as a loud speaker or the like), assembled thereon.

According to an aspect of the present invention, there is provided a head-mounted support device for carrying at least one un-inflated inflatable inner portion of an in-ear device thereon, said head-mounted support device comprising:

a main body for mounting on a user's head and having two side sections movably connected to one another for adjustment onto the user's head, each of said two side sections having an in-ear device receptacle for removably receiving an un-inflated inflatable inner portion of the in-ear device thereon;

each of said two side sections having a settable compound delivery device mounted on the main body, said settable compound delivery device including a self-injection device with a settable compound therein and an injection release mechanism connecting to the self-injection device;

wherein, for each of said two side sections, the self-injection device automatically injecting said settable compound into the un-inflated inflatable inner portion of the in-ear device via the in-ear device receptacle upon activation of said injection release mechanism by the user of said head-mounted support device.

Conveniently, the main body includes an adjusting mechanism for adjustably mounting said device onto a user's head.

Typically, the at least one settable compound delivery device is removably mounted onto said main body.

In one embodiment, the main body includes two side sections movably mounted to one another for adjustment onto the user's head.

Conveniently, each said section has a settable compound delivery device and an in-ear device receptacle.

Typically, each said settable compound delivery device is removably mounted onto respective said section.

According to another aspect of the present invention, there is provided a head-mounted settable compound delivery system kit comprising a head-mounted support device as above described, with at least one inner portion of an inflatable in-ear device.

Conveniently, the kit further includes an earphone wire assembly having a sound jack at a distal end thereof for connection to a sound device and at least one outer portion of an in-ear device mechanically connectable to the inflated inner portion thereof at a proximal end of the wire assembly.

Typically, the in-ear device outer portion is removably connectable to the in-ear device inflated inner portion.

Conveniently, the outer portion of an in-ear device includes an active component therein, and the active component is preferably removably mounted into the in-ear device outer portion.

According to a further aspect of the present invention, there is provided an earphone wire assembly comprising a sound jack at a distal end thereof for connection to a sound device and at least one outer portion of an in-ear device mounted at a proximal end thereof, the in-ear device outer portion being for connection to an inner portion of an in-ear device.

These and other advantages and objects will be apparent in view of the following detailed description in connection with the accompanying drawings.

BRIEF DESCRIPTION OF THE DRAWINGS

Further aspects and advantages of the present invention will become better understood with reference to the description in association with the following figures, in which similar references used in different figures denote similar components, wherein:

FIG. 3 is an enlarged exploded perspective view taken along line 3 of FIG. 2.

DETAILED DESCRIPTION OF THE PREFERRED EMBODIMENTS

Figure 1:
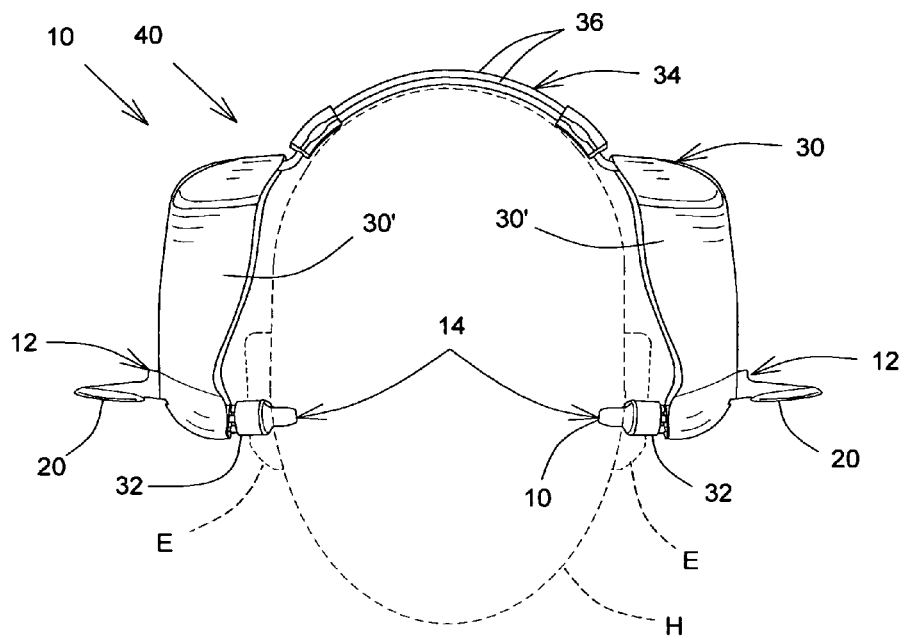
FIG. 1 is a schematic perspective view of a head-mounted support device for carrying a settable compound delivery system for inflatable in-ear devices in accordance with an embodiment of the present invention.

The device or system shown in the drawings and described below are examples which embody the invention. It should be noted that the scope of the invention is defined by the accompanying claims and not necessarily by specific features of the exemplary embodiments.

Figure 1A:
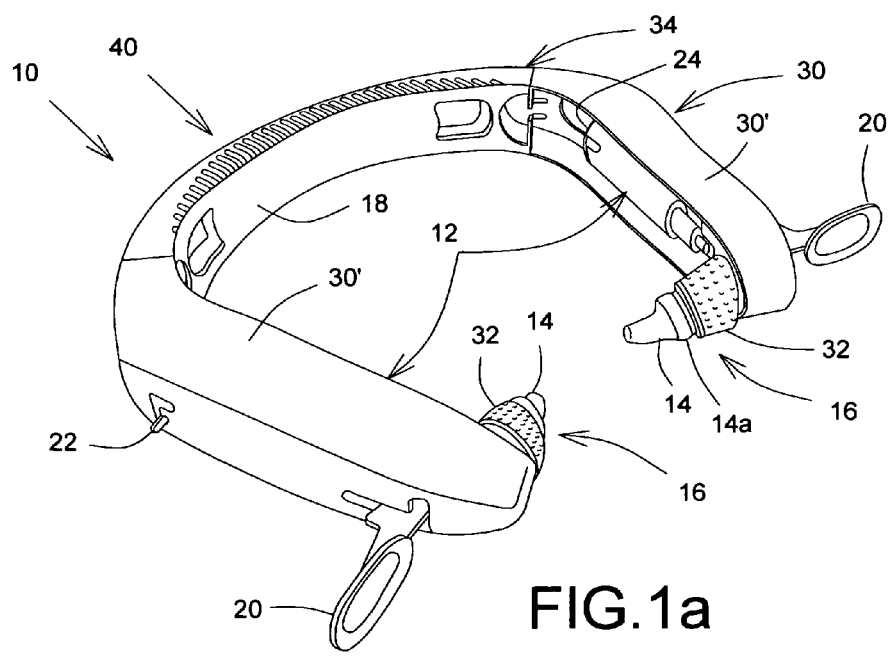
FIG. 1a is a perspective view of another embodiment of a head-mounted support device in accordance with the present invention.

Referring to FIGS. 1 and 1a, there are shown two embodiments of a head-mounted support device 10 for carrying at least one settable compound delivery device 12, typically with its pressure regulation mechanism (as best described in respective co-pending U.S. patent application Ser. No. 12/923,698 and Ser. No. 12/923,696 filed on Oct. 5, 2010 (both of which are herein incorporated in their entirety)) for at least one, preferably inner portion 14 (as best described in co-pending U.S. patent application Ser. No. 12/923,697 filed on Oct. 5, 2010 (which is also herein incorporated in its entirety)) of an inflatable in-ear device 16 in the form of a generally rigid adjustable headband support device or the like. The headband device 10 carries all the equipment required for a self injecting settable compound device 12 and is adapted to typically removably receive the left and right inflatable in-ear device inner portions 14 (typically referring to the portion reaching into the ear canal) thereon such that the user can take the in-ear device inner portions 14, ended with an interface retaining ring 14a (see FIGS. 2 and 3), off after fitting injection thereof. Although the support structure shown in FIGS. 1 and 1a is a headband device 10, any other structure could be considered without departing from the scope of the present invention, as long as the structure, typically positionable onto the user's head H in a manner to be substantially integral therewith, supports the settable compound delivery devices 12 along with the inflatable in-ear device inner portions 14. Before activating the self-injection devices 12, the user properly adjusts the position of the headband device 10 to ensure that the two un-inflated (or virgin) in-ear device inner portions 14 are properly positioned within the respective ear E, inside the ear canal (not shown).

The head-mounted device 10 allows for a proper orientation of the inflatable in-ear device(s) 16, or inner portion(s) 14 thereof, typically at a preferred frontward and upward angular orientation. In order to adapt to the different morphologies of different users, a restricted biased gimbal connection (not shown) could be considered between the main body 30 and the in-ear device receptacle 32 mounted thereon (see hereinbelow).

Furthermore, the head-mounted device 10 maintains the required target pressure on the in-ear device(s) 16, or inner portion(s) 14 thereof, during inflation thereof.

In order to improve the positioning of the in-ear devices 16, or the inner portions 14 thereof, the device 10 can include an in-situ sound delivery system (not shown) propagating sound through the in-ear devices 16, such that, for example, the user will know that a good positioning of the in-ear devices is achieved when the sound is the clearest possible.

The settable compound delivery device 12 shown in FIG. 1 and more specifically FIG. 1a includes, for each in-ear device 16, a pump mechanism, shown here in the form of a hinged lever 20 biasing a compression coil spring (not shown) or the like connected to a main piston (not shown), activatable by the user to apply pressure (typically between about 20 and 40 psi) inside the different chambers or compartments (not shown) of the two parts of the two-part compound (may typically have more than one compartment for each part) of the settable compound, via the main piston, prior to the injection thereof inside the in-ear device inner portion 14. An unlocking injection mechanism, typically one for each pump mechanism and shown here in the form of a rotating tab 22, allows the user to unlock the activation (injection release) mechanism, shown here as a push button 24 that essentially simultaneously perforates the walls of the different compartments for allowing the flow of the settable compound, to allow the user to start the self-injection delivery of the settable compound into the in-ear device inner portion 14. The unlocking injection mechanism 22 typically prevents the user from inadvertently starting the activation mechanism (pushing on the corresponding button 24) before the corresponding in-ear device inner portion 14 is properly positioned into the ear, and before the pump mechanism 20 has been operated. Although not illustrated, the operation of the pump mechanism could also include a release mechanism (not shown) that would release and allow operation of the unlocking injection mechanism 22 upon pressurizing the settable compound inside the compartments via the lever 20.

More specifically, the head-mounted support device 10 for carrying at least one un-inflated inflatable inner portion 14 of an in-ear device 16 thereon, includes a main body 30 adapted to mount on the head H of the user and that has at least one in-ear device receptacle 32, preferably two, to removably receive an un-inflated inflatable inner portion 14 of an in-ear device 16 thereon. The device 10 also includes at least one settable compound delivery device 12 mounted on the main body 30 for the delivery of settable compound to the inflatable in-ear inner portion 14 via the at least one in-ear device receptacle 32.

The main body 30 typically includes an adjusting mechanism 34, represented as two arcuate sections 36 slidably mounted to one another, or could also be a generally flexible elastic section of the body, to properly adjust the positioning of the device 10 onto the user's head H, and to maintain the required target pressure on the in-ear device 16, or inner portion 14 thereof, during injection of the settable compound therein. Typically, the settable compound delivery device 12 is removably mounted onto the main body 30 such that the body could be re-used to customize other sets of in-ear device inner portions 14.

As shown in FIGS. 1 and 1*a*, the main body 30 typically includes two side sections 30' movably connected to one another for adjustment onto the user's head H, with each section having a corresponding settable compound delivery device 12 and an in-ear device receptacle 32.

Figure 2:
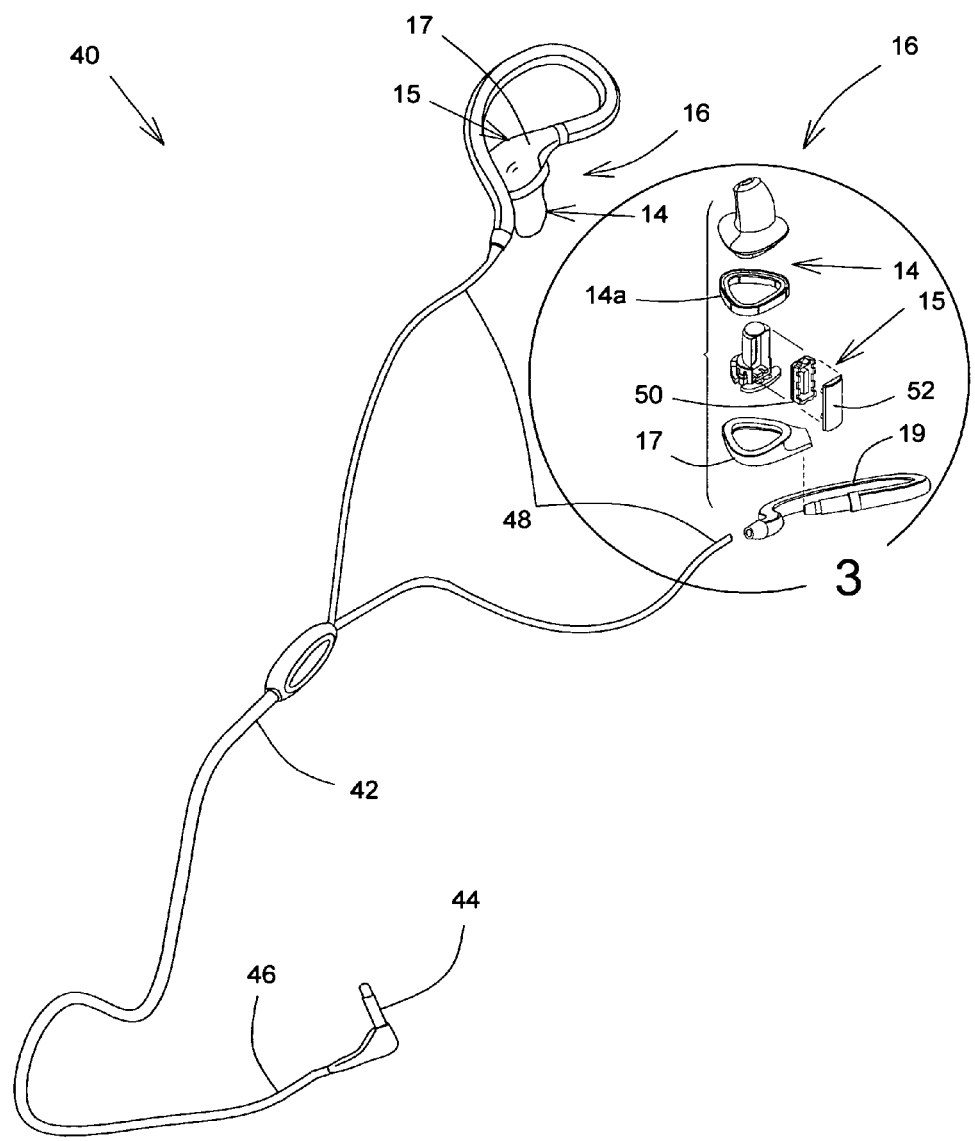
FIG. 2 is a perspective view of a customizable earphone wire assembly with inflatable in-ear devices in accordance with an embodiment of the present invention.

The present invention also refer to a head-mounted settable compound delivery system kit 40 for inflatable in-ear device 16, or inner portion 14 thereof, that includes the above described head-mounted support device 10, with at least one settable compound delivery device 12 and at least one in-ear device inflatable inner portion 14. The kit 40 typically includes an earphone wire assembly 42, as shown in FIG. 2, that has a sound jack 44 at a distal end 46 thereof for connection to a sound device (not shown) such as a MP3 music player or the like, and at least one, preferably two outer portions 15 of in-ear devices 16 mechanically connectable to the inflated inner portions 14 thereof at a proximal end 48 (left and right) of the wire assembly 42. Each outer portion 15 typically includes an outer cover 17 preferably carrying an outer ear hook 19 or the like to assist in maintaining the in-ear device 16 in the user's ear.

Typically, the in-ear device outer portion 15 is removably connectable to the in-ear device inflated inner portion 14 such that either one could be later replaced by a new one as required.

Furthermore, as best shown in FIG. 3, the outer portion 15 of an in-ear device 16 typically includes an active component 50 therein, such as a loudspeaker or the like, depending on the use of the in-ear device 16. In some applications, the active component 50 could be removably mounted into the in-ear device outer portion 15, typically with a protective cover 52, to allow for possible replacement thereof in case of malfunctioning or simply for a change of component 50 having different functions and/or characteristics.

The present invention also refers to the earphone wire assembly 42 as hereinabove described, having replaceable in-ear device inflatable inner portions 14, as well as interchangeable active components 50 of the in-ear device outer portion 15.

The support device 10 of the present invention may also integrate and/or carry the wire assembly 42, such as in a wiring chamber 18 (see FIG. 1*a*), for proper use of the in-ear devices 16 once custom-fitted using the settable compound delivery devices 12 as been done.

Although the present invention has been described with a certain degree of particularity, it is to be understood that the disclosure has been made by way of example only and that the present invention is not limited to the features of the embodiments described and illustrated herein, but includes all variations and modifications within the scope and spirit of the invention as hereinafter claimed.

We claim:

1. A head-mounted support device for carrying at least one un-inflated inflatable inner portion of an in-ear device thereon, said head-mounted support device comprising:
   a main body for mounting on a user's head and having two side sections movably connected to one another for adjustment onto the user's head, each of said two side sections having an in-ear device receptacle for removably receiving an un-inflated inflatable inner portion of said in-ear device thereon;
   each of said two side sections having a settable compound delivery device mounted on the main body, said settable compound delivery device including a self-injection device with a settable compound therein and an injection release mechanism connecting to the self-injection device;
   wherein, for each of said two side sections, the self-injection device automatically injecting said settable compound into the un-inflated inflatable inner portion of the in-ear device via the in-ear device receptacle upon activation of said injection release mechanism by the user of said head-mounted support device.

2. A head-mounted support device according to claim 1, wherein said main body includes an adjusting mechanism for adjustably mounting said head-mounted support device onto the user's head.

3. A head-mounted support device according to claim 1, wherein said settable compound delivery device is removably mounted onto said main body.

4. A head-mounted support device according to claim 1, wherein each said settable compound delivery device is removably mounted onto respective said section.

5. A head-mounted settable compound delivery system kit comprising:
   a head-mounted support device including a main body for mounting on a user's head and having two side sections movably connected to one another for adjustment onto the user's head, each of said two side sections having an in-ear device receptacle;
   each of said two side sections having an un-inflated inflatable inner portion of an in-ear device mountable on said in-ear device receptacle;
   each of said two side sections having a settable compound delivery device mounted on the main body, said settable compound delivery device including a self-injection device with a settable compound therein and an injection release mechanism connecting to the self-injection device;
   wherein, for each of said two side sections, the self-injection device automatically injecting said settable compound into the un-inflated inflatable inner portion of the in-ear device via the in-ear device receptacle upon activation of said injection release mechanism by the user of said head-mounted support device.

6. A kit according to claim 5, wherein said settable compound delivery device is removably mounted onto said main body.

7. A kit according to claim 5, wherein each said settable compound delivery device is removably mounted onto respective said section.

8. A kit according to claim 5, wherein said main body includes an adjusting mechanism for adjustably mounting said head-mounted support device onto the user's head.

* * * * *